(12) United States Patent
Auyoung (10) Patent No.: US 10,478,240 B2
(45) Date of Patent: Nov. 19, 2019

(54) DEVICE FOR PERFORMING A SURGICAL PROCEDURE AND METHODS OF USE

(71) Applicant: Medtronic Holding Company Sàrl, Tolochenaz (CH)

(72) Inventor: Bryan J. Auyoung, Santa Clara, CA (US)

(73) Assignee: Medtronic Holding Company Sàrl, Tolochenaz (CH)

( * ) Notice: Subject to any disclaimer, the term of this patent is extended or adjusted under 35 U.S.C. 154(b) by 736 days.

(21) Appl. No.: 15/043,692

(22) Filed: Feb. 15, 2016

(65) Prior Publication Data

US 2016/0157909 A1 Jun. 9, 2016

Related U.S. Application Data

(62) Division of application No. 13/760,876, filed on Feb. 6, 2013, now Pat. No. 9,295,510.

(51) Int. Cl.
*A61B 17/88* (2006.01)

(52) U.S. Cl.
CPC ...... *A61B 17/8805* (2013.01); *A61B 17/8811* (2013.01); *A61B 17/8855* (2013.01)

(58) Field of Classification Search
CPC .................. A61B 17/8805; A61B 17/8855
See application file for complete search history.

(56) References Cited

U.S. PATENT DOCUMENTS

| 4,773,393 | A | 9/1988 | Haber et al. |
| 5,843,116 | A | 12/1998 | Crocker et al. |
| 6,129,737 | A | 10/2000 | Hamilton et al. |
| 6,352,551 | B1 | 3/2002 | Wang |
| 6,364,900 | B1 | 4/2002 | Heuser |
| 6,416,457 | B1 | 7/2002 | Urick et al. |
| 6,488,653 | B1 | 12/2002 | Lombardo |
| 6,527,739 | B1 | 3/2003 | Bigus et al. |
| 6,544,224 | B1 | 4/2003 | Steese-Bradley |
| 8,221,349 | B2 | 7/2012 | Auyoung et al. |
| 2003/0130664 | A1 | 7/2003 | Boucher et al. |
| 2008/0249604 | A1* | 10/2008 | Donovan ........... A61B 17/8811 606/249 |
| 2009/0088788 | A1 | 4/2009 | Mouw |
| 2009/0254064 | A1 | 10/2009 | Boatman |
| 2009/0299327 | A1* | 12/2009 | Tilson ................ A61B 17/8816 604/500 |

(Continued)

FOREIGN PATENT DOCUMENTS

| DE | 10010467 A1 | 9/2001 |
| WO | 2006053312 A1 | 5/2006 |
| WO | 2008026888 A1 | 3/2008 |

*Primary Examiner* — Olivia C Chang (57) ABSTRACT

A device includes an outer member extending between a first end and a second end. The outer member comprises an inner surface defining a passage. The device includes an inflatable member having a first end extending from the second end of the outer member and a second end. The inflatable member includes an inner surface defining a chamber. The inner surface of the outer member is continuous with the inner surface of the inflatable member. The device includes an inner member having a first end positioned within the passage and a second end coupled to the second end of the inflatable member such that the inner member does not engage the inner surface of the outer member. Systems and methods are disclosed.

19 Claims, 3 Drawing Sheets

(56) References Cited

U.S. PATENT DOCUMENTS

2011/0106184 A1    5/2011    Sapida et al.
2011/0202064 A1    8/2011    O'Halloran et al.
2012/0197319 A1    8/2012    Auyoung et al.
2012/0197321 A1    8/2012    Donovan
2012/0296273 A1    11/2012    Arana et al.
2013/0144298 A1    6/2013    Choi

\* cited by examiner

DEVICE FOR PERFORMING A SURGICAL PROCEDURE AND METHODS OF USE

CROSS-REFERENCE TO RELATED APPLICATIONS

This application is a Divisional of U.S. patent application Ser. No. 13/760,876, filed on Feb. 6, 2013, which is incorporated herein by reference herein, in its entirety.

TECHNICAL FIELD

The present disclosure generally relates to medical devices for the treatment of musculoskeletal structures, and more particularly to a surgical system and method employing an inflatable bone tamp and bone filler material.

BACKGROUND

Extremity fractures of a calcaneus or other bone may be reduced percutaneously using inflatable bone tamps (IBTs). IBTs can be expensive to manufacture and require multiple components to be assembled prior to usage. IBTs may require platinum/Iridium markers to both indicate the orientation of an inflatable balloon in situ and for attaching the inflatable balloon to an inner stylet. This disclosure describes, inter alia, a device having a reduced amount of components and manufacturing steps, and therefore a lower cost of production over prior art technologies.

SUMMARY

Accordingly, a surgical system including an IBT device and method of use are provided. In one embodiment, in accordance with the principles of the present disclosure, the IBT device includes an outer member extending between a first end and a second end. The outer member comprises an inner surface defining a passage. The device includes an inflatable member having a first end extending from the second end of the outer member and a second end. The inflatable member includes an inner surface defining a chamber. The inner surface of the outer member is continuous with the inner surface of the inflatable member. The IBT device includes an inner member having a first end positioned within the passage and a second end coupled to the second end of the inflatable member such that the inner member is spaced apart from the inner surface of the outer member.

In one embodiment, in accordance with the principles of the present disclosure, a method includes creating an access path to a bone, inserting the IBT device discussed in the preceding paragraph into the access path to position the inflatable member within the bone, and inflating the inflatable member to compress a portion of the bone and create a cavity.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for bone repair. It is envisioned that the disclosed surgical system and method may be employed in applications such as for correction of fractures, depressions and breaks. For illustrative purposes, the disclosed device, system, and method shall be described in the context of positioning an inflatable body and the use of bone void filler in a vertebral body of a patient to treat vertebral compression fractures, although the disclosed devices, systems and methods can be used to treat other conditions.

In one embodiment, the disclosed system includes an IBT including a balloon and balloon tubing sheathed with a hypotube. The hypotube is biocompatible and rigid. In some embodiments, the hypotube comprises a metal, such as, for example, stainless steel or a nylon jacket. In one embodiment, the hypotube includes thin walls, which restrict the inflation of the balloon tubing disposed within. It is envisioned that the thickness of the wall of the hypotube may be varied depending upon the requirements of a particular application. The hypotube provides column strength along the length of the hypotube to allow for the axial translation of the catheter through the cannula. The disclosed device eliminates the need for proximal balloon bonding, a co-extruded outer shaft, a removable stylet and/or a Y-adaptor. The configuration of the disclosed device also eliminates the need for an inner shaft assembly extending the entire length of the device.

In one embodiment, the length of a distal tip of the balloon tubing may be varied. In one embodiment, the length of the distal tip of the balloon is approximately 2 mm. In some embodiments, the length of the balloon may be more or less than 2 mm, depending upon the requirements of a particular application. Without the need for an inner shaft tethering the distal tip of the balloon tubing, more longitudinal growth may be encountered. In one embodiment, this is minimized by providing a balloon having a larger initial diameter or maximized by providing a balloon having a narrow initial diameter. In one embodiment, a luer connector replaces the Y-adaptor included with conventional IBTs, as a removable stylet is not included in the disclosed devices. In one embodiment, the stylet has a smaller outside diameter than the hypotube and does not extend the entire length of the device, but in other embodiments, the stylet may extend the entire length of the device. The smaller outside diameter of the stylet relative to the hypotube makes marker bands unnecessary given that the step down from the hypotube to the balloon and/or the stylet supporting the balloon would be adequate to visualize the position of the balloon prior to inflation. Visualizing the position of the balloon prior to inflation aids in determining placement of the balloon for inflation.

In one embodiment, the disclosed system includes a device having a metal or nylon hypotube, which may be compounded with radio-opaque filler to aid in fluoroscopic visualization, loaded over a proximal end of a balloon tubing. A short stylet, such as, for example, a wire can be inserted in a balloon engaged with the balloon tubing from a distal end of the balloon tubing. The distal end of the balloon tubing is then bonded to the distal end of the wire to provide additional column strength to support the balloon during delivery to a surgical site, such as, for example, a bone void. In one embodiment, the wire can be used for fluoroscopic imaging of the balloon prior to inflation of the balloon, potentially so as to eliminate the need for marker bands. In one embodiment, a luer connector is then attached to the proximal end of the balloon tubing. The luer connector may also be replaced by a Tuohy-Borst connector. It is envisioned that a proximal end of the luer connector can be attached to an inflation device to inflate the balloon. In some embodiments, the disclosed device, including the balloon, is capable of withstanding pressures exceeding 700 psi. It is envisioned that the disclosed devices minimize the number of components and the number of manufacturing steps over prior art technologies such that the disclosed devices can be manufactured at 50-70% less cost relative to prior art technologies, and therefore reduced overall costs, while avoiding any significant negative impact on performance.

It is contemplated that one or all of the components of the surgical system may be disposable, peel-pack, and/or pre-packed sterile devices. One or all of the components of the surgical system may be reusable. The surgical system may be configured as a kit with multiple sized and configured components.

It is envisioned that the present disclosure may be employed to treat bones, and in particular extremity bones such as the calcaneus. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there are illustrated components of a surgical system 20 in accordance with the principles of the present disclosure.

The components of system 20 can be fabricated from biologically acceptable materials suitable for medical applications, including metals, synthetic polymers, ceramics and bone material and/or their composites, depending on the particular application and/or preference of a medical practitioner. For example, the components of system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening systems and/or instruments, as described herein.

System 20 is employed, for example, with an open, mini-open or minimally invasive surgical technique to attach move or apply pressure to a bone fragment, fracture or surface, such as, in treating calcaneus fractures. System 20 includes a device, such as, for example, an inflatable bone tamp 22 for performing a surgical procedure. Device 22 includes an outer member, such as, for example, balloon tubing 24 extending between a first end 26 and a second end 28. In one embodiment, end 26 engages a fitting, such as, for example, a luer connector 30. It is envisioned that end 26 may be configured to engage other types of fittings, such as, for example a Touhy-Borst connector, a Y-adapter, or an L-adapter, depending upon the requirements of a particular application. A balloon 32 extends from end 28, as will be described.

Balloon tubing 24 comprises an inner surface 34 defining a passage 36. Passage 36 has a length and a width. In one embodiment, passage 36 has a uniform width along the entire length of passage 36. In some embodiments, the width of passage 36 is variously configured, such as, for example, irregular, non-uniform, offset, staggered, and/or tapered, depending upon the requirements of a particular application. In one embodiment, passage 36 has an arcuate cross section configuration. In some embodiments, passage 36 has alternate cross section configurations, such as, for example, oval, oblong, triangular, square and/or polygonal, depending on a particular application.

Balloon tubing 24 comprises a compliant material configured to radially and longitudinally expand when passage 36 exceeds a threshold internal pressure. In one embodiment, balloon tubing 24 comprises any type of inflatable material, including non-compliant materials (e.g., many nylon and polyethylene materials), semicompliant materials (e.g., many polyurethane materials), compliant materials (e.g., latex rubber), or any combination thereof. It is envisioned that balloon 32 can be made from a non-elastic material, such as, for example, polyethylene tetraphthalate (PET), nylon, Kevlar® or other medical inflatable body/balloon materials; semi-elastic materials, such as, for example, silicone, rubber, thermoplastic rubbers and elastomers; or elastic materials such as, for example, latex or polyurethane. In one embodiment, balloon 32 is made from the same material as balloon tubing 24. In some embodiments, balloon 32 is made from a different material than balloon tubing 24.

Balloon 32 includes a first end 38 extending from end 28 of balloon tubing 24 such that end 28 and end 38 are continuous. End 38 is disposed adjacent to a second end 60 of a hypodermic tube 56, as will be described. End 40 is coupled to a stylet 66 positioned within passage 36, as will also be described.

Balloon 32 includes a wall 42 having an inner surface 44 and an outer surface 46. Inner surface 44 defines a chamber, such as, for example, a fillable cavity 48. Inner surface 44 is continuous with inner surface 34. Balloon 32 has a larger diameter D1 than a diameter D2 of balloon tubing 24 when balloon 32 is in an inflated configuration. It is contemplated that balloon 32 and balloon tubing 24 have similar diameters along their lengths when balloon 32 is in an uninflated configuration. In one embodiment, diameter D1 of balloon 32 is non-uniform along the length of balloon 32.

Fillable cavity 48 is configured to be in communication with passage 36 such that an inflation material, such as, for example, gas or air, is inserted through passage 36 and into cavity 48 to balloon 32 to move balloon 32 from the uninflated configuration to the inflated configuration. The inflation material is removed from balloon 32 through passage 36 to move balloon 32 from the inflated configuration to the uninflated configuration. Outer surface 46 is configured to engage and a apply force to tissue, such as, for example, cancellous bone when balloon 32 is in the inflated configuration. It is contemplated that outer surface 46 may have surface configurations to enhance engagement with tissue, such as, for example, smooth, rough, arcuate, undulating, dimpled and/or textured, according to the requirements of a particular application. It is envisioned that all or only a portion of balloon 32 may have cross section configurations, such as, for example, oval, oblong, triangular, square, polygonal, irregular, uniform, non-uniform, offset, staggered, and/or tapered depending on a particular application.

In one embodiment, wall 42 has a non-uniform height such that wall 42 has a greater height portion disposed between ends 38, 40 of balloon 32 than at end 38 and/or end 40. The greater height portion of wall 42 defines a reduced-diameter junction 50 defining two lobes 52, 54 disposed on opposite sides of junction 50 and having a greater height than junction 50 such that balloon 32 has a dual-lobed (peanut shaped) configuration depicted for exemplary purposes. It is envisioned that balloon 32 may have one or a plurality of lobes. In some embodiments, balloon 32 ovoid, spheroid, cylindrical, or any other shape.

Tube 56 extends between a first end 58 and a second end 60. End 58 is connected to luer connector 30. End 60 is disposed adjacent balloon 32. Tube 56 includes an inner surface 62 defining a passage 64. Passage 64 has a uniform width configured for disposal of balloon tubing 24 such that tube 56 surrounds balloon tubing 24. Tube 56 is configured to be substantially rigid such that it resists radial expansion when balloon 32 is in the inflated configuration. The substantially rigid configuration of tube 56 provides column strength to support balloon tubing 24 during translation of balloon tubing 24 and/or balloon 32 through passage 64 for delivery to a surgical site, such as, for example, a bone defect. Tube 56 has a substantially cylindrical shape and a substantially arcuate cross section configuration. In some embodiments, tube 56 may be variously configured and dimensioned, such as, for example, oval, oblong triangular, square, polygonal, irregular, uniform, non-uniform, offset, staggered, and/or tapered, depending upon the requirements of a particular application. In one embodiment, tube 56 comprises stainless steel. It is contemplated that tube 56 can be made of various materials, such as, for example, nitinol, nylon, peek, and high-density polyethylene (HDPE).

In one embodiment, stylet 66 is a stainless steel wire. In one embodiment, stylet is a nitinol wire. Additionally, in other embodiments stylet 66 is nylon or a polymer. Stylet 66 has an elongated cylindrical shape and an arcuate cross section configuration. It is contemplated that stylet 66 may be variously configured and dimensioned, such as, for example, oval, oblong, triangular, square, polygonal, irregular, uniform, non-uniform, offset, staggered, and/or tapered, depending on a particular application. Stylet 66 extends throughout fillable cavity 48 and at least a portion of passage 36. In one embodiment, stylet 66 extends through fillable cavity 48 and the entire length of passage 36 such that stylet 66 has a length that is greater than the length of balloon tubing 24. Stylet 66 extends between a first end 68 and a second end 70. End 68 is positioned within passage 36 and passage 64. In one embodiment, end 70 is coupled to end 40 by a thermal heat seal such that stylet 66 is spaced apart from inner surface 34.

In one embodiment, end 70 includes radiopaque markers to aid in determining when end 40 projects from tube 56 such that balloon 32 can be delivered to a surgical site. In one embodiment, device 22 is free of any radiopaque marker materials. In one embodiment, stylet 66 has a length that is less than one half of a length of balloon tubing 24 such that stylet 66 extends less than half way of the length of passage 36 of balloon tubing 24.

Luer connecter 30 is positioned at ends 58, 26 of tube 56 and balloon tubing 24, respectively. It is contemplated that materials, such as, for example, saline, contrast or water can be deployed through luer connector 30. Luer connector 30 is adapted for attachment to a medium delivery device configured for delivering a medium used to inflate balloon 32. In one embodiment, the luer connector is replaced by a Touhy-Borst connector.

In operation, balloon 32 is oriented in the desired position within a patient with the aid of a medical imaging device. The proper positioning of balloon 32 can be attained by determining the location of ends 38 and 40 of balloon 32. End 38 of balloon 32 is located by viewing the step down between end 60 of tube 56 and end 68 of stylet 66. End 40 of balloon 32 is located by viewing end 70 of stylet 66. After balloon 32 has been oriented in the desired position, an inflation medium, such as, for example, saline is injected through luer connecter 30 and into end 26 of balloon tubing 24. The saline travels through the length of balloon tubing 24 causing balloon tubing 24 to radially expand within passage 64 of tube 56. Balloon tubing 24 radially expands until an outer surface of balloon tubing 24 contacts inner surface 62 of tube 56, which prevents further radial expansion of balloon tubing 24. After the saline passes end 68 of stylet 66 and end 38 of balloon 32, the saline begins to fill fillable cavity 48. As saline is injected into device 22, the pressure within fillable cavity 48 increases causing wall 42 of balloon 32 to expand about stylet 66.

In assembly, operation and use, system 20 is employed with a surgical procedure, such as, for example, a correction or treatment of bone fractures. It is contemplated that one or all of the components of system 20 can be delivered or implanted as a pre-assembled device or can be assembled in situ.

For example, as shown in FIGS. 1-4, system 20, described above, can be employed with a surgical correction treatment of an applicable condition or injury of an affected portion of calcaneus bone, bones of the feet or hands, bones of the spine, bones of the arms and legs, etc. and other areas within a body. It is envisioned that system 20 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 20 is determined according to the configuration, dimension and location of a selected section of the bone fracture and the requirements of a particular application.

In use, to treat a fracture, a medical practitioner obtains access to a surgical site including fractured bone in any appropriate manner, such as through incision and retraction of tissues. In one embodiment, a tool, such as, for example, a drill is employed to remove bone tissue to provide an access path to a repair site, such as, for example, bone.

An incision is made in the body of a patient and a cutting instrument creates a surgical pathway for delivery of components of system 20 to a surgical site, such as, for example, a bone void. A preparation instrument can be employed to prepare tissue surfaces, as well as for aspiration and irrigation of a surgical region according to the requirements of a particular surgical application.

Device 22 is inserted through the incision, with balloon tubing 24 disposed in tube 56 and is navigated to the surgical site with the aid of a medical imaging device. In one embodiment, device 22 may be delivered to the surgical site though a cannula by first inserting the cannula into the incision and then inserting tube 56 with balloon tubing 24 disposed therein into the cannula. Balloon 32 can be positioned in the desired location, such as, for example, in the bone void or adjacent the bone void by determining the location of ends 38, 40 of balloon 32. End 38 of balloon 32 is located by viewing the step down between end 60 of tube 56 and end 68 of stylet 66. End 40 of balloon 32 is located by viewing end 70 of stylet 66. After balloon 32 has been oriented in the desired position at the desired location, an inflation medium, such as, for example, saline is injected through luer connecter 30 and into end 26 of balloon tubing 24. The saline travels through the length of balloon tubing 24 causing balloon tubing 24 to radially expand within passage 64 of tube 56. Balloon tubing 24 radially expands until it makes contact with inner surface 62 of tube 56, resisting further radial expansion of balloon tubing 24. After the saline passes end 68 of stylet 66 and end 38 of balloon 32, the saline begins to fill fillable cavity 48. As more saline is injected into device 22, the pressure within fillable cavity 48 increases causing wall 42 of balloon 32 to expand about stylet 66.

Balloon 32 in its inflated configuration compresses a portion of the bone and creates a cavity. When a desired cavity size has been achieved, balloon 32 is deflated and device 22 is withdrawn from the access path. A cannula is inserted through the incision and is positioned such that a distal end of the cannula is in or adjacent the cavity created in the bone by balloon 32. A delivery nozzle is inserted into the cannula and bone filler material, such as, for example, bone cement is injected into the cavity from the delivery nozzle.

Figure 1:
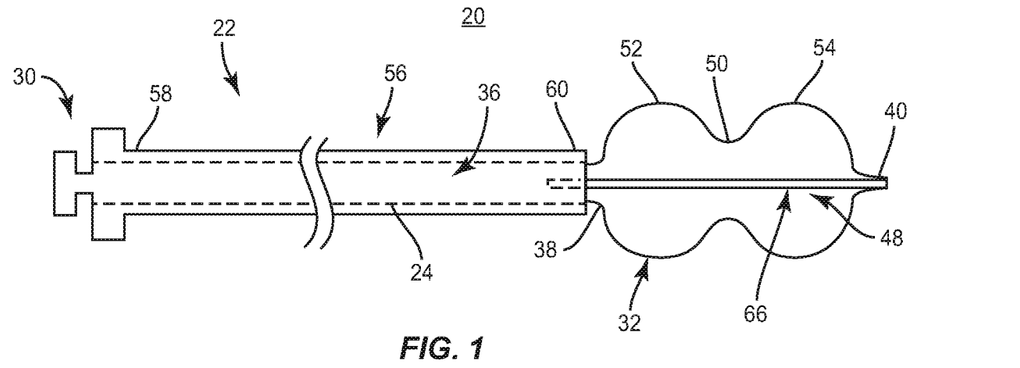
FIG. 1 is a break away, side view, in part cross section, of components of a surgical system in accordance with the principles of the present disclosure.
Figure 2:
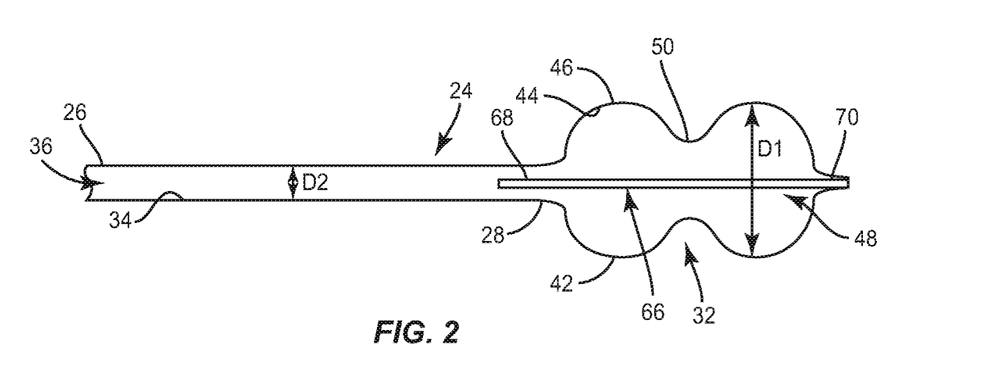
FIG. 2 is a break away, side view of components of the surgical system shown in FIG. 1.
Figure 3:
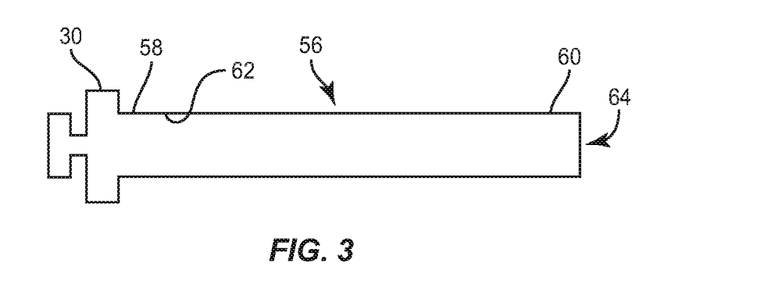
FIG. 3 is side view of components of the surgical system shown in FIG. 1.
Figure 4:
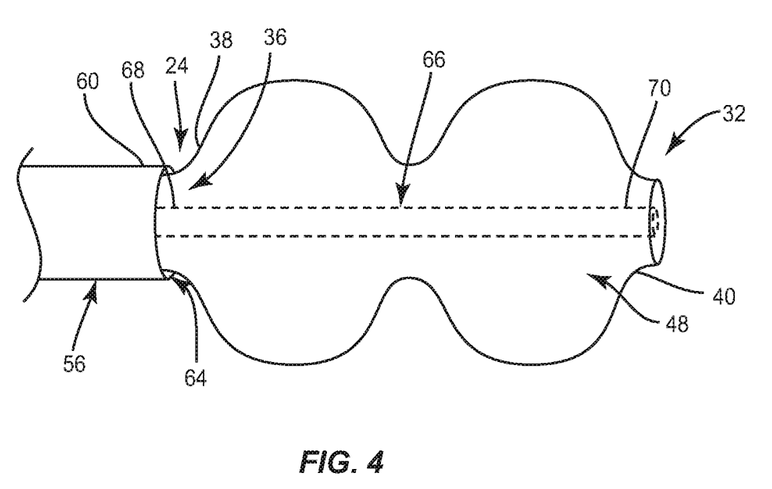
FIG. 4 is a break away, perspective view of components of the surgical system shown in FIG. 1.
Figure 5:
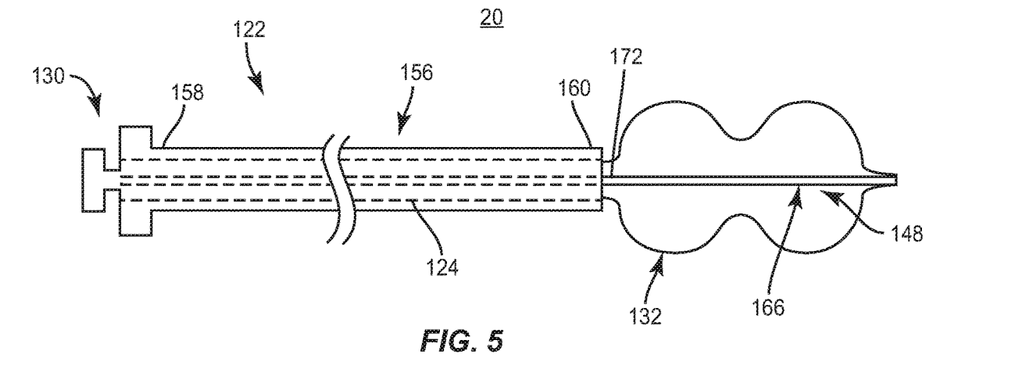
FIG. 5 is a break away, side view, in part cross section, of one embodiment of components of a surgical system in accordance with the principles of the present disclosure.
Figure 6:
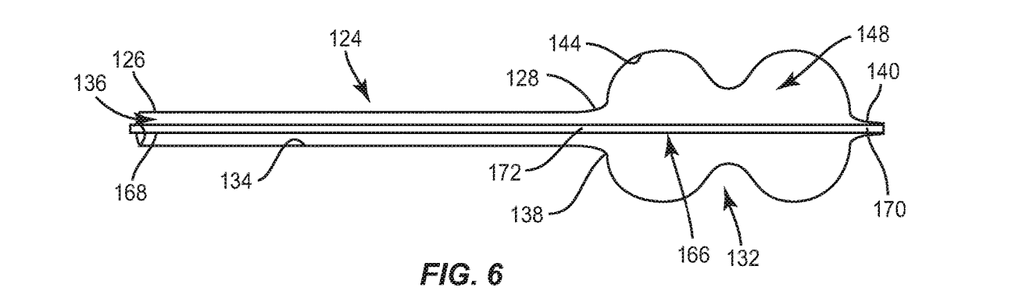
FIG. 6 is a side view of components of the surgical system shown in FIG. 5.
Figure 7:
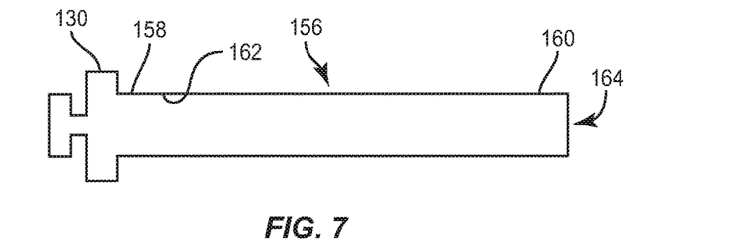
FIG. 7 is a side view of components of the surgical system shown in FIG. 5.

In one embodiment, as shown in FIGS. 5-7, system 120 includes a device, 122, similar to device 22 described above with reference to FIGS. 1-4. Device 122 includes an outer member, such as, for example, a balloon tubing 124, similar to balloon tubing 24 described above. Balloon tubing 124 extends between a first end 126 and a second end 128. End 126 is connected to a fitting, such as, for example, a luer connector 130. Balloon tubing 124 comprises an inner surface 134 defining a passage 136. Passage 136 has a length defined by the length of balloon tubing 124. Passage 136 has a uniform width throughout the entire length of passage 136.

Device 122 includes an inflatable member, such as, for example, a balloon 132, similar to balloon 32 described above. Balloon 132 includes a first end 138 and a second end 140. End 138 of balloon 132 is disposed adjacent to a second end 160 of a jacket 156, as will be described. Balloon 132 extends from end 128 of balloon tubing 124 such that end 128 of balloon tubing 124 and end 138 of balloon 132 are integrally connected or monolithically formed. Balloon 132 includes an inner surface 144 that defines a chamber, such as, for example, a fillable cavity 148, similar to fillable cavity 48 described above. Inner surface 134 of balloon tubing 124 is continuous with inner surface 144 of balloon 132.

Device 122 includes a hollow structure, such as, for example, jacket 156. Jacket 156 comprises nylon. Balloon tubing 124 is disposed with jacket 156. Jacket 156 extends between a first end 158 and a second end 160. End 158 is connected to a luer connector 130. End 160 is disposed adjacent to balloon 132. Jacket 156 includes an inner surface 162 defining a passage 164. Passage 164 has a uniform width configured for disposal of balloon tubing 124 such that jacket 156 surrounds balloon tubing 124.

Device 122 includes an inner member, such as, for example, a stylet 166, similar to stylet 66 described above. Stylet 166 comprises a wire made from stainless steel wire or nitinol. Stylet 166 has a length that is at least as long the length of balloon tubing 124 such that stylet 166 extends the entire length of passage 136 of balloon tubing 124. In one embodiment, stylet has a length that is longer than the length of balloon tubing 124 such that stylet extends the entire length of balloon tubing 124 and the entire length of balloon 132. Stylet 166 includes a first end 168 and a second end 170. End 168 is disposed at end 126 of balloon tubing 124. End 170 is coupled to end 140 of balloon 132 by a thermal heat seal such that stylet 166 does not engage inner surface 134 of balloon tubing 124.

Stylet 166 includes an intermediate portion 172 disposed between end 160 of jacket 156 and end 138 of balloon 132. In one embodiment, portion 172 includes radiopaque markers for identification under x-ray, fluoroscopy, CT or other imaging techniques to aid in locating end 138 of balloon 132 in situ. In one embodiment, end 170 of stylet 166 includes radiopaque markers that aid in locating end 140 of balloon 132 in situ. In one embodiment, device 122 is free of any radiopaque marker materials.

In one embodiment, systems 20,120 include an agent, which may be disposed, packed or layered within, on or about the components and/or surfaces of systems 20,120, such as, for example, balloon tubing 24, 124 and/or balloons 32, 132. It is envisioned that the agent may include bone growth promoting material, such as, for example, bone graft to enhance bone growth to repair a defect at a surgical site, such as, for example, a bone void.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage, with the aid of systems 20,120. Upon completion of the procedure, the surgical instruments and assemblies are removed. The opening drilled in to the bone is filled with a bone cement to provide support for the repaired bone, and the incision is closed.

It is contemplated that systems 20,120 include balloons, such as, for example, balloons 32, 132, that are single or multi-layered balloons, where each balloon layer has the same diameter and/or wall thickness, is comprised of the same material or materials having substantially identical mechanical properties, and has the same degree of molecular orientation in the body portion of the balloon. In some embodiments, the layers of balloons 32, 132 have different thicknesses, materials, and/or degrees of molecular orientations upon deflation, while at the same time having equivalent size, mechanical properties, and/or orientation upon inflation.

It is contemplated that systems 20,120 include balloons, such as, for example, balloons 32, 132, can be adapted to withstand the particular stresses, pressures, and deformities to which they might be placed under when inflated to return the calcaneus surface to a proper orientation. For example, because the top layer might be exposed to sharp objects (such as calcified plaque, bone, bone spurs, or other natural protrusions within a patient's body), the top layer could be made from a more compliant material that is scratch and puncture resistant. In the case of a multi-layer balloon, the outer layer is made from a more compliant material that is scratch and puncture resistant and the inner layers of the multi-layer balloon, which are generally not exposed to sharp objects, made from a less compliant material with a higher burst strength.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment.

What is claimed is:

1. A method comprising:
providing a device comprising an expandable first tubing portion, an expandable second tubing portion, a transition portion, and a substantially rigid outer member, the first tubing portion and the second tubing portion being joined by the transition portion, the first tubing portion extending through a first passage extending through the substantially rigid outer member, and the second tubing portion extending outwardly from the substantially rigid outer member;

creating an access path to a bone;

inserting the device into the access path to position at least a first inflatable lobe portion and a second inflatable lobe portion of the second tubing portion within the bone;

passing an inflation medium through a second passage formed by an inner surface of the first tubing portion, through a third passage formed by an inner surface of the transition portion, and into a chamber formed by an inner surface of the second tubing portion, the inner surfaces of the first tubing portion, the transition portion, and the second tubing portion being continuous with one another;

preventing the first tubing portion from expanding via contact of an outer surface of the first tubing portion with an inner surface of the substantially rigid outer member;

inflating the first inflatable lobe portion and the second inflatable lobe portion of the second tubing portion from uninflated positions to inflated positions with the inflation medium by expanding the first inflatable lobe portion and the second inflatable lobe portion; and compressing a portion of the bone and create a cavity via inflation of the first inflatable lobe portion and the second inflatable lobe portion.

2. The method of claim 1, further comprising an inner member extending through the first tubing portion, the transition portion, and the second tubing portion, the inner member being connected to a distal end of the second tubing portion.

3. The method of claim 1, further comprising delivering a bone filler material into the cavity through the access path.

4. The method of claim 3, wherein creating the access path comprises docking a cannula with the bone, and delivering the bone filler material comprises inserting a delivery nozzle into the cannula and injecting the bone filler material into the cavity from the delivery nozzle.

5. The method of claim 1, further comprising: deflating the first inflatable lobe portion and the second inflatable lobe portion; and withdrawing the device from the access path.

6. The method of claim 1, wherein, after inflation of the first inflatable lobe portion and the second inflatable, the first inflatable lobe portion and the second inflatable lobe portion have diameters substantially equal to one another.

7. The method of claim 6, wherein the second tubing portion includes a connecting portion between the first inflatable lobe portion and the second inflatable lobe portion, the connecting portion having a reduced-diameter less than diameters of the first inflatable lobe portion and the second inflatable lobe portion after inflation of the first inflatable lobe portion and the second inflatable lobe portion.

8. A method comprising:

providing a device comprising an expandable first tubing portion, an expandable second tubing portion, a transition portion, and a substantially rigid outer member, the first tubing portion and the second tubing portion being joined by the transition portion, the first tubing portion extending through a first passage extending through the substantially rigid outer member, and the second tubing portion extending outwardly from the substantially rigid outer member;

creating an access path to a bone;

inserting the device into the access path to position at least a first inflatable lobe portion and a second inflatable lobe portion of the second tubing portion within the bone;

passing an inflation medium through a second passage formed by an inner surface of the first tubing portion, through a third passage formed by an inner surface of the transition portion, and into a chamber formed by an inner surface of the second tubing portion, the inner surfaces of the first tubing portion, the transition portion, and the second tubing portion being continuous with one another;

preventing the first tubing portion from expanding via contact of an outer surface of the first tubing portion with an inner surface of the substantially rigid outer member;

inflating the first inflatable lobe portion and the second inflatable lobe portion of the second tubing portion from uninflated positions to inflated positions by expanding the first inflatable lobe portion and the second inflatable lobe portion with the inflation medium, while simultaneously limiting inflation of the transition portion in comparison to the first inflatable lobe portion and the second inflatable lobe portion, the first inflatable lobe portion and the second inflatable lobe portion having diameters substantially equal to one another and greater than a diameter of the transition portion; and compressing a portion of the bone and create a cavity via inflation of the first inflatable lobe portion and the second inflatable lobe portion.

9. The method of claim 8, further comprising an inner member extending through the first tubing portion, the transition portion, and the second tubing portion, the inner member being connected to a distal end of the second tubing portion.

10. The method of claim 8, further comprising delivering a bone filler material into the cavity through the access path.

11. The method of claim 10, wherein creating the access path comprises docking a cannula with the bone, and delivering the bone filler material comprises inserting a delivery nozzle into the cannula and injecting the bone filler material into the cavity from the delivery nozzle.

12. The method of claim 8, further comprising: deflating the first inflatable lobe portion and the second inflatable lobe portion; and withdrawing the device from the access path.

13. A method comprising:

providing a device comprising:

a substantially rigid outer member having a proximal first end, an opposite distal second end, and a first passage extending between the proximal first end and the distal second end, an inner member having a first end and an opposite second end;

an expandable first tubing portion having a proximal first end and an opposite distal second end, the first tubing portion comprising an outer surface and an inner surface, the first tubing portion extending through the first passage, and the inner surface of the first tubing portion defining a second passage;

an expandable second tubing portion having a proximal first end and a distal second end, the second tubing portion including a first inflatable lobe portion, a second inflatable lobe portion, and connecting portion connecting the first inflatable lobe portion and the second inflatable lobe portion, and an inner surface defining a chamber within the first inflatable lobe portion, the second inflatable lobe portion, and the connecting portion;

a transition portion connecting the first tubing portion and the second tubing portion, the transition portion including an inner surface being continuous with the inner surface of the first tubing portion and the inner surface of the second tubing portion;

creating an access path to a bone;

inserting the device into the access path to position at least the first inflatable lobe portion and the second inflatable lobe portion of the second tubing portion within the bone;

inflating at least the first inflatable lobe portion and the second inflatable lobe portion of the second tubing portion from uninflated positions to inflated positions; and compressing a portion of the bone and create a cavity via inflation of the first inflatable lobe portion and the second inflatable lobe portion, wherein the substantially rigid outer member prevents expansion of the first tubing portion during inflation of the first inflatable lobe portion and the second inflatable lobe portion, and the first end of the inner member is positioned within the first passage and the second end of the inner member is connected to the distal second end of the second tubing portion such that the inner member does not engage the inner surface of the first lubing portion.

14. The method of claim 13, further comprising delivering a bone filler material into the cavity through the access path.

15. The method of claim 14, wherein creating the access path comprises docking a cannula with the bone, and delivering the bone filler material comprises inserting a delivery nozzle into the cannula and injecting the bone filler material into the cavity from the delivery nozzle.

16. The method of claim 13, further comprising: deflating the first inflatable lobe portion and the second inflatable lobe portion; and withdrawing the device from the access path.

17. The method of claim 13, wherein the first passage has a length defined by a length of the substantially rigid outer member, and the inner member has a length that is greater than the length of the substantially rigid outer member.

18. The method of claim 13, wherein, after inflation, the first inflatable lobe portion and the second inflatable lobe portion have diameters substantially equal to one another.

19. The method of claim 18, wherein the connecting portion has a reduced-diameter between the first inflatable lobe portion and the second inflatable lobe portion, the reduced-diameter being less than diameters of the first inflatable lobe portion and the second inflatable lobe portion after inflation of the first inflatable lobe portion and the second inflatable lobe portion.

\* \* \* \* \*